US00PP10382P

United States Patent [19]

Bos

[11] Patent Number: Plant 10,382

[45] Date of Patent: May 5, 1998

[54] VRIESIA PLANT NAMED 'PROMINENT'

[76] Inventor: Henny Bos, Hoefslag 1,, 2641 ZZ Pijnacker, Netherlands

[21] Appl. No.: 766,340

[22] Filed: Dec. 16, 1996

[51] Int. Cl.[6] ..... A01H 5/00

[52] U.S. Cl. ..... Plt./88.8

[58] Field of Search ..... Plt./88.8

*Primary Examiner*—James R. Feyrer

*Attorney, Agent, or Firm*—C. A. Whealy

[57] ABSTRACT

A distinct cultivar of Vriesia plant named 'Prominent', characterized by its bi-colored leaves that have green margins and off-white centers.

1 Drawing Sheet

1

The present invention relates to a new and distinct cultivar of Vriesia plant, botanically known as *Vriesia poelmanii*, and hereinafter referred to by the cultivar name 'Prominent'.

The new cultivar was discovered in 1982 by the inventor in Pijnacker, The Netherlands, in a controlled environment as a naturally occurring mutation in a large population of plants of the cultivar 'Vulcana' (not patented). The new cultivar was discovered as a single plant within this population of plants of the cultivar 'Vulcana' and was distinguished by its bi-colored leaves compared to the solid green leaves of the cultivar 'Vulcana'.

Asexual propagation of the new cultivar at Pijnacker, The Netherlands, has shown that the unique features of this new Vriesia plant are stable and reproduced true to type in successive generations of asexual propagation.

The new Vriesia has not been observed under all possible environmental conditions. The phenotype may vary somewhat with variations in environment such as temperature and light intensity, without, however, any variance in genotype. The following observations, measurements and comparisons describe plants grown in Pijnacker, The Netherlands, in 13-cm containers in a glass greenhouse with average day and night temperatures of 20C.

The expression of green and off-white bi-colored leaves has been repeatedly observed and this characteristic is determined to be a characteristic unique to 'Prominent' and distinguishes 'Prominent' as a new and distinct cultivar.

The accompanying colored photograph illustrates the overall appearance of the new cultivar, showing the colors as true as it is reasonably possible to obtain in colored reproductions of this type.

The photograph comprises a side perspective view of a typical potted plant of 'Prominent'.

Actual colors may appear slightly different from the colors in the photograph due to light reflectance.

In the following description, color references are made to The Royal Horticultural Society Colour Chart except where general terms of ordinary dictionary significance are used. The following observations and measurements describe plants grown in Pijnacker, The Netherlands, under commercial practice in a glass-covered greenhouse with average night and day temperatures of 20C.

Botanical classification: Vriesia cultivar 'Prominent'.

Parentage: Naturally occurring mutation of the cultivar 'Vulcana' (not patented).

Propagation: By divisions.

Plant description:

2

*Plant shape:*—Rosette of leaves, outwardly arching, upright flower spike, plants symmetrical.

*Growth habit.*—Erect when young, becoming outwardly arching as leaves develop. Appropriate for 10 to 20-cm containers.

*Plant height.*—About 45 cm from soil level to top of leaf plane.

*Plant vigor.*—Moderately vigorous.

*Crop time.*—15 to 18 months are usually require from planting of a young plant to a finished 13-cm container.

*Rooting habit.*—Central tap root.

Rooting time.—About 30 days at a temperature of 22C.

*Foliage description.*—Quantity: 20 to 30 per 13-cm plant. Leaf shape: Linear, sword-like. Leaf length: 25 to 45 cm. Leaf width: 2.5 to 3.5 cm. Margin: Entire. Leaf tip: Acute. Leaf texture: Leathery, smooth, glabrous. Leaf color: Young foliage, upper surface: Margin: 159C. Center: 137A. Young foliage, lower surface: Margin: 159C. Center: 137C. Mature foliage, upper surface: Margin: 159C. Center: 137C. Mature foliage, lower surface: Margin: 159C. Center: 137C.

Flower description:

*Flower appearance:*—Similar to plants of the cultivar Vulcana, no other differences. Flattened spikes of bright red bracts and yellow flowers.

*Flower arrangement.*—Branched inflorescence with 10 to 40 single bell-shaped flowers with showy bracts. Plants flower yearround.

*Flower longevity.*—Inflorescences may continue to flower for 3 to 4 months, individual flowers last about 2 days. Flowers persistent.

*Flower diameter.—About* 7 mm.

*Flower depth (height).*—About 2 cm.

*Flower color.*—Bright yellow, 7B.

*Calyx.*—Shape: Like a pear. Size: 2.5 to 3.5 cm.

*Stamens.*—Quantity: 8. Anther shape: Cylindrical. Anther size: About 4.5 mm. Anther color: 7B. Pollen color: Slightly darker than 7B.

*Pistils.*—Quantity: 1. Stigma shape: Flat. Style length: About 2.5 cm.

Disease resistance: No resistance or susceptibility to diseases has been noted.

It is claimed:

1. A new and distinct cultivar of Vriesia plant named 'Prominent', as illustrated and described.

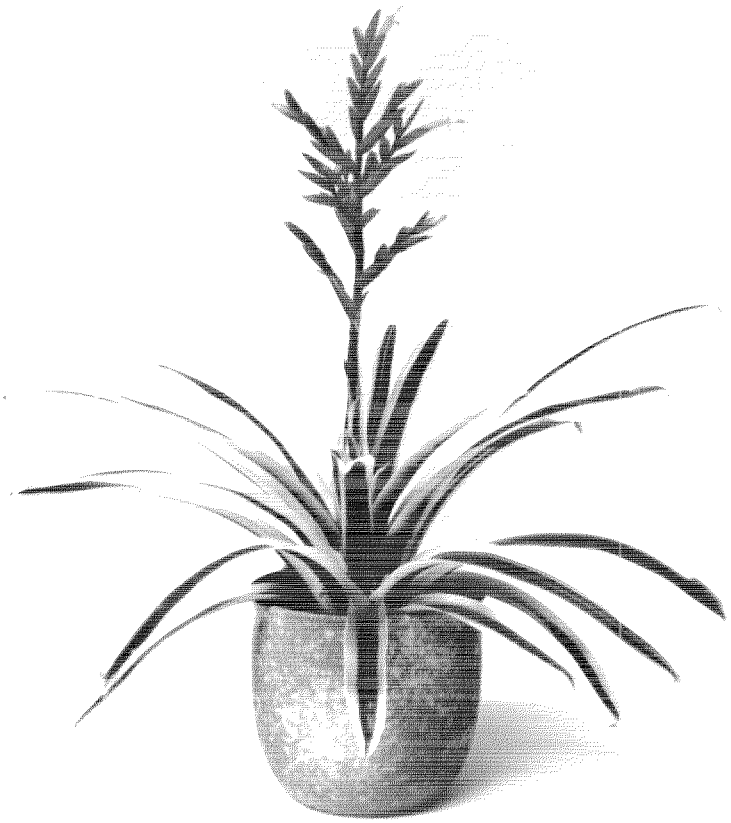

* * * * *